United States Patent [19]

Ethridge

[11] Patent Number: 5,400,797
[45] Date of Patent: Mar. 28, 1995

[54] NASAL STETHOSCOPE

[76] Inventor: Michael Ethridge, P.O. Box 2152, Batesville, Ark. 72503

[21] Appl. No.: 192,595

[22] Filed: Feb. 7, 1994

[51] Int. Cl.$^6$ .............................................. A61B 5/08
[52] U.S. Cl. ........................................................ 128/716
[58] Field of Search ............ 128/716, 719, 773, 200.26, 128/202.27, 207.18, 200.24, 206.11, 204.12, 207.13, 912, 725; 607/135

[56] References Cited

U.S. PATENT DOCUMENTS

| | | | |
|---|---|---|---|
| 3,530,850 | 9/1970 | Edwards | 128/716 |
| 5,097,827 | 3/1992 | Izumi | 128/204.12 |
| 5,113,857 | 5/1992 | Dickerman et al. | 128/205.11 |

*Primary Examiner*—Lee S. Cohen
*Assistant Examiner*—Brian M. Green

[57] ABSTRACT

A nasal stethoscope including a nostril tube for insertion into a human nostril, a spring-type clip affixed to the nostril tube, and a pad affixed to a first jaw member of the spring-type clip. The spring-type clip is movable between a closed position and an open position. The pad is interposed between the nostril tube and the first jaw member. A connector tube is affixed to an end of the nostril tube opposite an open end of the nostril tube. An earpiece tube can be removably connected to an end of the connector tube opposite the nostril tube. The clip has a second jaw member directly affixed to an outer surface of the nostril tube. The clip extends in generally parallel relationship to a longitudinal axis of the nostril tube. The first jaw member has an arm extending outwardly therefrom so as to move the clip from the closed position to the open position. The first and second jaw members have tapered ends narrowing toward an end of the nostril tube.

19 Claims, 1 Drawing Sheet

NASAL STETHOSCOPE

TECHNICAL FIELD

The present invention relates to apparatus for monitoring the breathing of a human being. More particularly, the present invention relates to nasal stethoscopes for audio observation of human breathing.

BACKGROUND ART

Breath sounds generated by humans are of two primary types, namely, tracheal (also referred to as bronchial) breath sounds which are generated by the passage of air through the major airways between the mouth and the lungs, and vesicular breath sounds which are normally detected over most of the chest of a human. These sounds have heretofore generally been observed by placing a stethoscope over the major airways in the case of bronchial sounds or other areas of the chest in the case of vesicular sounds and listening to the sounds directly. Observations of breathing patterns have also been assisted through the use of electronic stethoscopes which amplify the breath sounds.

Abnormal breath sounds can frequently provide significant information about pulmonary and associated abnormalities which are not readily detected by other means. The major types of abnormal breath sounds have been described by various observers.

In many circumstances, it is necessary to monitor the sounds of human breathing which come directly through the nasal passageways. However, in the past, there has been no convenient way to monitor such breath sounds without great difficulty. The conventional method of monitoring breath sounds is the use of the conventional precordial stethoscope. This type of stethoscope uses a double-sided adhesive pad so as to hold it in place on the trachea or upper chest area of the patient. However, this adhesive often proves to be ineffective. It often falls off when the patient is turned to a lateral, sitting or prone position. Another method of listening to breath sounds is just to tape the end of earpiece tubing around the nose or mouth. This tape, however, has a tendency to come off. This will cause the dislodging of the tubing. Also, tape is often abrasive to facial skin. Other methods of observing breathing patterns require close visual and/or hands-on contact with the patient throughout the procedure. This is confining, difficult, and time consuming.

In the past, various U.S. patents have issued with respect to devices that are used for the monitoring of breathing sounds. For example, U.S. Pat. No. 3,990,435, issued on Nov. 9, 1976, to R. L. Murphy teaches an apparatus for detecting breathing abnormalities which forms a visual display of the breath sounds of a patient using a time-expanded scale. This allows the apparatus to delineate the differentiating sonic characteristics of the sounds. This is designed so as to monitor breathing abnormalities, such as coarse and fine rales, as well as abnormalities such as rhonchi. The device also serves to provide early diagnosis of diseases such as bronchities and bronchial pneumonia.

U.S. Pat. No. 4,600,015, issued on Jul. 15, 1986, to Evans et al. teaches an apparatus for monitoring patient functions, particularly the depth of anesthesia. This device employs an oseophageal probe having a balloon located in the patient's oesophagus so as to provoke contractions thereof. A gas cylinder or pump is provided so as to apply air or saline solution to the balloon. A sensor is provided for detecting sounds indicative of oesophageal contraction.

U.S. Pat. No. 4,949,716, issued on Aug. 21, 1990, to D. Chenoweth provides a nasal intubation adjunct. When the patient is intubated, this device allows for the monitoring of breathing patterns. A stethoscope headset is attached to the device so as to provide an audible reference and for the monitoring of patient inspiration and expiration.

U.S. Pat. No. 5,056,513, issued on Oct. 15, 1991, to G. Boutin provides a micro air-wave detection device for breathing monitoring and surveillance. This device includes a tube having a ball disposed therein with minimal clearance. The tube is disposed in a horizontal or slightly inclined position and is connected to a conduit which picks up the pressure variation of a nasal respirator. The detection of the to-and-fro movement of the ball provides a monitor of the breathing patterns.

U.S. Pat. No. 5,245,995, issued on Sep. 21, 1993, to Sullivan et al. discloses a device for the monitoring of breathing during sleep. This apparatus includes a nosepiece for sealed air communication with the patient's respiratory system. An air communication line extends from the air source to the nosepiece. A sound transducer is adapted to be in sound communication with the patient's respiratory system. A feedback system is provided for controlling the output pressure of the air source in response to an output from the transducer so as to increase the output air pressure from the air source. The sound transducer includes a pressure transducer which can detect respiratory parameters such as the rate of breathing, inhaled air flow volume, and inhaled air flow rate.

In general, all of these patented devices are quite complicated systems for the monitoring of breathing patterns. Often, in the hospital setting, it is only necessary for the physician to occasionally monitor the breathing patterns of the patient. Ideally, the monitoring of such breathing patterns could be accomplished without disturbing the patient or be accomplished without disturbing the patient's sleep.

It is an object of the present invention to provide a nasal stethoscope that can be securely affixed and retained in position about the nostrils of the patient.

It is another object of the present invention to provide a nasal stethoscope which is not intrusive or disturbing to the patient.

It is another object of the present invention to provide a nasal stethoscope which is relatively easy to use, simple to manufacture, and inexpensive.

These and other objects and advantages of the present invention will become apparent from a reading of the attached specification and appended claims.

SUMMARY OF THE INVENTION

The present invention is a nasal stethoscope that comprises a nostril tube for insertion into a nostril, a spring-type clip affixed to the nostril tube, and a pad affixed to a first jaw member of the clip and interposed between the nostril tube and the first jaw member. The clip is movable between a closed position and an open position.

The nostril tube includes a nostril tube member having an open end received within the human nostril. This open end is adjacent to the pad. A connector tube is affixed to an end of the nostril tube member opposite this open end. The connector tube has a means thereon for attachment to an earpiece tube. The means of the connector tube is specifically a tip which is affixed to an end of the connector tube opposite the nostril tube. The tip is insertable into an interior of the earpiece tube. An earpiece tube is removably connected to this tip. The connector tube has an end which is affixed over an outer diameter of the nostril tube member. The connector tube has an interior passageway which is coaxial with an interior of the nostril tube member. The nostril tube member and the connector tube are of a soft rubber material. The tip is of a plastic material.

The clip of the nasal stethoscope of the present invention is, preferably, an alligator clip. The clip includes a second jaw member which is directly affixed to an outer surface of the nostril tube. The second jaw member has an end aligned with an open end of the nostril tube. The clip extends in parallel relationship to a longitudinal axis of the nostril tube. The first jaw member has an arm extending outwardly therefrom. This arm serves to move the clip from the closed position to the open position. The first jaw member is pivotally connected to the second jaw member. A spring is positioned at the area of pivotal connection so as to urge the clip toward the closed position. Each of the first and second jaw members has tapered ends narrowing toward an end of the nostril tube.

The pad extends outwardly beyond an end of the first jaw member and an end of the nostril tube. The pad is of a soft rubber material. The clip serves to exert constant applied pressure to a surface of the pad when the clip is in the closed position.

DETAILED DESCRIPTION OF THE INVENTION

Figure 1:
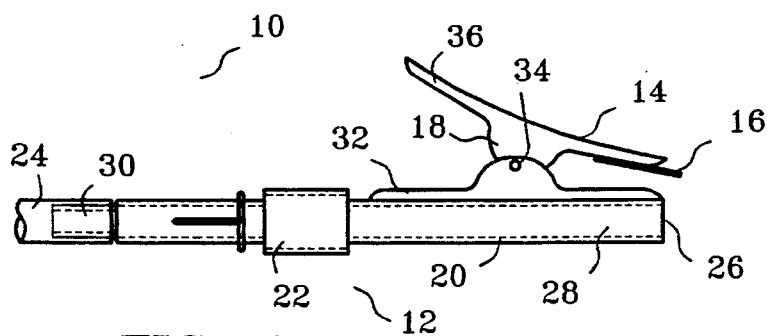
FIG. 1 is a side elevational view of the nasal stethoscope of the present invention as shown in its closed position.

Referring to FIG. 1, there is shown at 10 the nasal stethoscope in accordance with the preferred embodiment of the present invention. The nasal stethoscope can include a tube 12, a spring-type clip 14, and a pad 16. The tube 12 is designed for insertion into a human nostril. As can be seen, the spring-type clip 14 is affixed to a surface of the tube 12. The pad is affixed to a first jaw member 18 of the clip 14. The pad 16 is interposed between the first jaw member 18 of the clip 14 and the tube 12.

The tube 12 includes a nostril tube 20, a connector tube 22, and an earpiece tube 24. The nostril tube 20 has an open end 26 generally adjacent to the pad 16 and to the end of the first jaw member 18 of the clip 14. The open end 26 will be received within the human nostril when the clip 14 is affixed to the exterior surface of the nose. As can be seen, the nostril tube 12 has an interior passageways 28 which extends from the open end 26 to the end received by the connector tube 22. The clip 14 extends in generally parallel relationship with the longitudinal axis of the nostril tube 20. The interior passageway 28 is of a generally constant diameter. The nostril tube 20 is of a soft, flexible, rubber material.

The connector tube 22 is affixed to an end of the nostril tube 20 opposite the open end 26. The connector tube 22 has one end which is affixed over an outer diameter of the nostril tube 20 beyond an end of the clip 14. The connector tube 22 has an interior passageway which is coaxial with interior passageway 28 of the nostril tube 20. The connector tube 22 can be adhesively or mechanically affixed over the exterior surface of the nostril tube 20. The connector tube 22 is also of a soft rubber material. It is within the scope of the present invention that the connector tube 22 can be integrally formed with the nostril tube 20. The connector tube 22 has a tip 30 affixed to an end of the connector tube 22 opposite the nostril tube 20. This tip 30 is insertable into the interior passageway of the earpiece tube 24. The tip 30 can be of a plastic material. The earpiece tube 24 has an end which elastically and removably engages the tip 30 of the connector tube 22. The earpiece tube 24 extends outwardly beyond the connector tube 22 for a considerable distance so as to allow sounds to pass to the ear of the clinician. The earpiece tube 24 is also of a soft rubber material. The detachable connection between the earpiece tube 24 and the tip 30 of the connector tube 22 allows the monitoring to take place as necessary without undue disturbance of the patient. The earpiece tube 24 can simply be placed over the tip 30 so as to allow for the monitoring of the patient.

The clip 14 is an alligator clip. Experimentation has found that the alligator clip is the preferable type of clip 14. The alligator clip facilitates the ability to lead the tubing from the alligator clip to the earpiece of the clinician such that the earpiece tube can be securely fitted in place. The tapered end of such an alligator clip 14 allows for minimal obstruction of the nostrils to which it is attached. The pad 16 is not abrasive to the skin around the nose area of the patient. The alligator clip 14 can be easily manufactured and applies very consistent pressure between its jaws 18 and 32. Experimentation has found that the use of an alligator clip 14 is superior for keeping its grip on the nostril when placed into position. Neither the weight of the earpiece tube, nor the patient's position, seems to affect the firm, but gentle, grip of the alligator clip 14 onto the patient's nostrils.

Other types of designs, such as the single-sided clip (similar to a ball point pin clip), a clothes pin-type of clip, and loop clips have proven to be less effective. The single-sided clip was found to be inferior due to its grip of a nostril. A clothespin-type of clip was too bulky within the nostril and was obstructive to air flow. The loop-type clips are more difficult to secure to the nostrils and also are more difficult to secure to the tube which runs to the earpiece. These loop-type clips were also too bulky in the nostril area. Therefore, it was found that the alligator-type clip, with the narrow tapered tip, fits well into the nostril area without obstructing airflow.

In FIG. 1, it can be seen that the clip 14 has a first jaw member 18 and a second jaw member 32. The first jaw member 18 is pivotally connected at 34 to the second jaw member 32. A spring is positioned at the pivotal connection 34 so as to urge the clip 14 into its closed position, as shown in FIG. 1. The first jaw member 14 has an arm 36 which extends outwardly therefrom. The arm serves to move the clip 14 from the closed position (shown in FIG. 1) to the open position (shown in FIG.

2). Whenever compressive pressure is applied to the outer surface of the arm 36, the first jaw member 18 will pivot with respect to the second jaw member 32 so as to open the jaws for the purpose of placing the clip 14 onto the nose of the patient.

It can be seen that the second jaw member 32 is directly affixed to an outer surface of the nostril tube 20. The second jaw member has an end which is aligned with the open end 26 of the nostril tube 20. It can further be seen that the clip 14 extends in generally parallel relationship to a longitudinal axis of the nostril tube 20.

The pad 16 is affixed to the first jaw member 18 and extends outwardly beyond an end of the first jaw member 18. The pad 16 is of a soft rubber material. The pad 16 has an end which also extends outwardly beyond the edge 26 of the nostril tube 20. The pad 16 is interposed between the jaws 18 and 32 of the clip 14.

Figure 2:
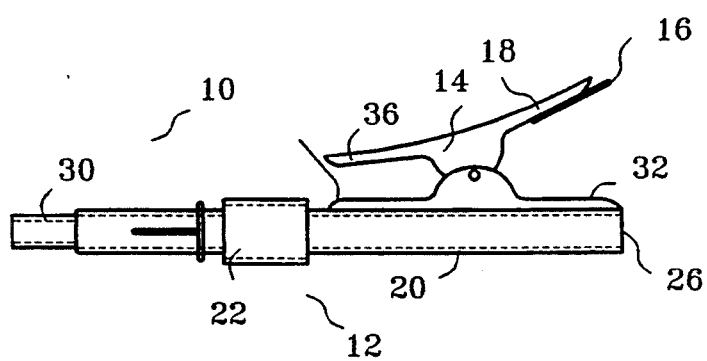
FIG. 2 is a side elevational view of the nasal stethoscope of the present invention as shown in its open position.

FIG. 2 illustrates the nasal stethoscope 10 of the present invention with the clip 14 illustrated in its open position. As can be seen, in the open position, a compressive force has been applied to the arm 36 of the first jaw member 18. This causes the arm 36 to approach the arm 40 of the second jaw member 32. As a result, the pad 16 will move away from the second jaw member 32. This causes the opening defined by the area between the pad 16 and the second jaw member 32 to be wide enough to accommodate the side of the nostril of the nose. This will allow the edge 26 of the nostril tube 20 to be properly inserted into the nostril of the patient. After the insertion has been completed, compressive forces are released from the arm 36 so as to allow the pad 16 to move toward the second jaw member 32.

Figure 3:
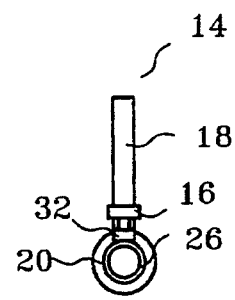
FIG. 3 is an end view of the nasal stethoscope of the present invention.

In FIG. 3, it can be seen that the clip 14 has a first jaw member 18 which tapers toward the end 26 of the nostril tube 20. The second jaw member 32 is affixed to an outer surface of the nostril tube 20. The pad 16 is shown as interposed between the first jaw member 18 and the second jaw member 32.

Figure 4:
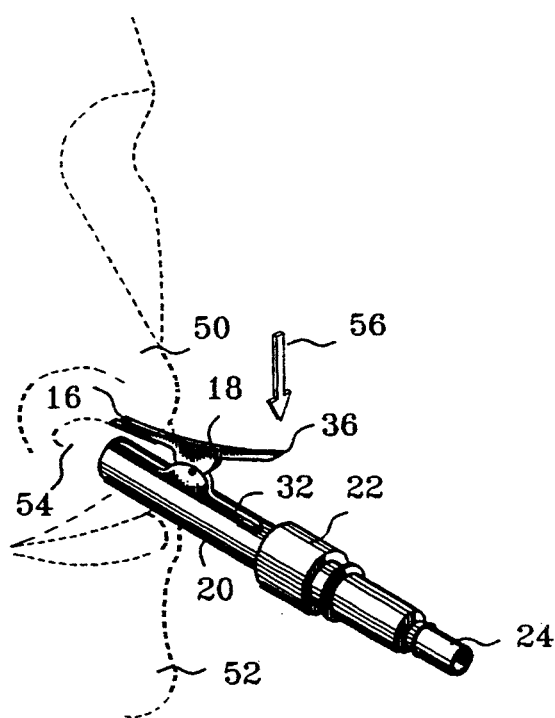
FIG. 4 is a perspective view of the nasal stethoscope of the present invention as applied to the nostril passageways of a patient.

FIG. 4 illustrates the manner in which the nasal stethoscope 10 is affixed to the nose 50 of a patient 52. As can be seen, the nostril tube 20 is positioned for insertion into the nostril 54 of the nose 50. Prior to insertion, a compressive force 56 (illustrated by the arrow in FIG. 4) is applied to the top surface of the arm 36 of the first jaw member 18. As a result, the pad 16 will separate from the second jaw member 32. The nostril tube 20 is then in a position to be inserted into the nostril 54 of the nose 50. After this insertion is completed, then the compressive force 56 is removed from the arm 36. This will cause the pad 16 and the first jaw member 18 to engage in compressive contact with an exterior surface of the nose 50. The second jaw member 32, and the nostril tube 20, will be in contact with an inner surface of the nostril 50. The earpiece tube 24 is connected to the connector tube 22 so as to allow the clinician to examine the breathing patterns of the patient 52. The nasal stethoscope 10 will remain in position during the examination and following the examination.

The major advantage of the nasal stethoscope 10 of the present invention is that it will not fall off or become dislodged when the patient is in a lateral, sitting or prone position. The nasal stethoscope 10 of the present invention is disposable and serves for a one-time patient use only. No clean up or sterilizing is required following use. The nasal stethoscope 10 of the present invention allows for hand-free monitoring. The nasal stethoscope 10 of the present invention is very easy to use and inexpensive to manufacture. The soft rubber pad 16 (currently used for respiratory therapy) has been proven to be non-abrasive and gentle to the patient's nostrils. The present invention can be useful in procedures such as colonoscopies, bronchoscopies, extensive dental work, and other surgeries that require the patient to be in a prone position while under sedation or spinal anesthesia.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A nasal stethoscope comprising:
   a nostril tube means for insertion into a nostril;
   a spring-type clip affixed to said nostril tube means, said spring-type clip having a first jaw member, said clip movable between a closed position and an open position; and
   a pad affixed to said first jaw member, said pad interposed between said nostril tube means and said first jaw member.

2. The nasal stethoscope of claim 1, said nostril tube means comprising:
   a nostril tube having an open end adjacent said pad, said open end adapted to be received within the nostril.

3. The nasal stethoscope of claim 2, said nostril tube means further comprising:
   a connector tube affixed to an end of said nostril tube opposite said open end, said connector tube having means thereon for attachment to an earpiece tube.

4. The nasal stethoscope of claim 3, said means of said connector tube being a tip affixed to an end of said connector tube opposite said nostril tube, said tip insertable into an interior of an earpiece tube.

5. The nasal stethoscope of claim 3, said nostril tube means further comprising:
   an earpiece tube removably connected to said means of said connector tube.

6. The nasal stethoscope of claim 5, said connector tube having an end affixed over an outer diameter of said nostril tube, said connector tube having an interior passageway coaxial with an interior of said nostril tube.

7. The nasal stethoscope of claim 4, said nostril tube and said connector tube being of a soft rubber material, said tip being of a plastic material.

8. The nasal stethoscope of claim 1, said spring-type clip being an alligator clip.

9. The nasal stethoscope of claim 1, said spring-type clip having a second jaw member directly affixed to an outer surface of said nostril tube means.

10. The nasal stethoscope of claim 9, said second jaw member having an end aligned with an open end of said nostril tube means, said spring-type clip extending in parallel relationship to a longitudinal axis of said nostril tube means.

11. The nasal stethoscope of claim 9, said first jaw member having an arm means extending outwardly therefrom, said arm means for moving said clip from said closed position to said open position.

12. The nasal stethoscope of claim 11, said first jaw member pivotally connected to said second jaw member, said clip having a spring positioned at the pivotal connection so as to urge said clip to said closed position.

13. The nasal stethoscope of claim 9, each of said first and second jaw members having tapered ends narrowing toward an end of said nostril tube means.

14. The nasal stethoscope of claim 1, said pad extending outwardly beyond an end of said first jaw member and an end of said nostril tube means, said pad being of a soft rubber material.

15. The nasal stethoscope of claim 1, said spring-type clip exerting constant applied pressure to a surface of said pad when in said closed position.

16. A nasal stethoscope comprising:
   a nostril tube having an open end;
   a connector tube affixed to an end of said nostril tube opposite said open end, said connector tube having means thereon for attachment to an earpiece tube; and
   a spring-type clip affixed to said nostril tube, said spring-type clip having a first jaw member, said clip movable between a closed position and an open position, said spring-type clip having a second jaw member directly affixed to an outer surface of said nostril tube, said second jaw member having an end aligned with the open end of said nostril tube, said spring-type clip extending in parallel relationship to a longitudinal axis of said nostril tube, each of said first and second jaw members having tapered ends narrowing toward the open end of said nostril tube.

17. The nasal stethoscope of claim 16, further comprising:
   a pad affixed to said first jaw member, said pad interposed between said nostril tube and said first jaw member.

18. A nasal stethoscope comprising:
   a nostril tube means for insertion into a human nostril; and
   a spring-type clip affixed to said nostril tube means, said spring-type clip having a first jaw member, said clip movable between a closed position and an open position, said spring-type clip having a second jaw member directly affixed to an outer surface of said nostril tube means, said first jaw member having an arm means extending outwardly therefrom, said arm means for moving said clip from said closed position to said open position, said first jaw member pivotally connected to said second jaw member, said clip having a spring positioned at the pivotal connection of said first jaw member with said second jaw member so as to urge said clip to said closed position, each of said first and second jaw members having tapered ends narrowing toward an end of said nostril tube means.

19. The nasal stethoscope of claim 18, further comprising:
   a pad affixed to said first jaw member, said pad interposed between said first jaw member and said second jaw member, said pad being of a soft rubber material.

* * * * *